United States Patent
Fukuma et al.

(10) Patent No.: US 9,662,013 B2
(45) Date of Patent: May 30, 2017

(54) OPHTHALMIC MICROSCOPE

(71) Applicant: KABUSHIKI KAISHA TOPCON, Itabashi-ku (JP)

(72) Inventors: Yasufumi Fukuma, Wako (JP); Kazuhiro Oomori, Setagaya-ku (JP); Satoshi Yamamoto, Saitama (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 0 days.

(21) Appl. No.: 15/049,317

(22) Filed: Feb. 22, 2016

(65) Prior Publication Data

US 2016/0278636 A1 Sep. 29, 2016

(30) Foreign Application Priority Data

Mar. 27, 2015 (JP) ................................. 2015-065696

(51) Int. Cl.
*A61B 3/14* (2006.01)
*A61B 3/13* (2006.01)

(52) U.S. Cl.
CPC ................ *A61B 3/132* (2013.01); *A61B 3/14* (2013.01)

(58) Field of Classification Search
CPC .................................. A61B 3/14; A61B 3/132

USPC .......................... 351/206, 205, 200, 368, 362
See application file for complete search history.

(56) References Cited

U.S. PATENT DOCUMENTS 7,628,490 B2 * 12/2009 Nakamura ............. A61B 3/135
351/214
2008/0079901 A1 4/2008 Nakamura

FOREIGN PATENT DOCUMENTS

JP 2008-86435 4/2008

* cited by examiner

*Primary Examiner* — Tuyen Tra
(74) *Attorney, Agent, or Firm* — Oblon, McClelland, Maier & Neustadt, L.L.P.

(57) ABSTRACT

According to one embodiment, an ophthalmic microscope includes an illumination system, a pair of light-receiving systems, and a first mechanism. The illumination system is configured to irradiate a subject's eye with illumination light. Each of the light-receiving systems includes a first objective lens and a first imaging device, and is configured to guide return light of the illumination light returning from the subject's eye to the first imaging device through the first objective lens. The objective optical axes of the light-receiving systems are not parallel to each other. The first mechanism is configured to move the light-receiving systems relative to each other to change an angle formed by the objective optical axes of the light-receiving systems.

16 Claims, 9 Drawing Sheets

OPHTHALMIC MICROSCOPE

CROSS-REFERENCE TO RELATED APPLICATION

This application is based upon and claims the benefit of priority from Japanese Patent Application No. 2015-065696, filed 27 Mar. 2015; the entire contents of which are incorporated herein by reference.

FIELD

Embodiments described herein relate generally to an ophthalmic microscope.

BACKGROUND

Various types of microscopes are used in the ophthalmic field to observe an enlarged view of the eye. Examples of the ophthalmic microscopes include slit lamp microscopes, surgical microscopes, and the like. Some ophthalmic microscopes include an imaging device to capture images of the eye and a binocular optical system to provide binocular disparity for stereoscopic vision.

The ophthalmic microscope is used in the observation of both the anterior segment (the cornea, sclera, conjunctiva, etc.) and the posterior segment (the retina, optic nerve, etc.) of the eye. Although, in general, an auxiliary optical member such as a front lens is additionally used to observe the posterior segment of the eye, if the pupil of the subject's eye is constricted or is small, an observation light flux is blocked by the iris, and it is often the case that the binocular observation cannot be performed suitably. This is likely to occur when the stereo angle of the binocular optical system is large. Meanwhile, information on the depth direction is important in particular to observe the anterior eye segment, and it is necessary to obtain an observation image having a three-dimensional appearance. This requires a sufficiently large stereo angle. In consideration of these circumstances, in the typical conventional ophthalmic microscope, a prism is placed in an observation light path to switch the stereo angle (see, for example, Japanese Unexamined Patent Application Publication No. 2008-86435).

However, the mechanism for changing the stereo angle using a prism is very large, which inevitably increases the size of the ophthalmic microscope. Moreover, the conventional ophthalmic microscope is not able to suitably change the stereo angle. For example, in the conventional ophthalmic microscope, the adjustment range of the stereo angle is narrow, and the fine adjustment cannot be performed.

SUMMARY

The embodiments are intended to provide an ophthalmic microscope capable of suitably changing the stereo angle.

According to one embodiment, an ophthalmic microscope includes an illumination system, a pair of light-receiving systems, and a first mechanism. The illumination system is configured to irradiate a subject's eye with illumination light. Each of the light-receiving systems includes a first objective lens and a first imaging device, and is configured to guide return light of the illumination light returning from the subject's eye to the first imaging device through the first objective lens. The objective optical axes of the light-receiving systems are not parallel to each other. The first mechanism is configured to move the light-receiving systems relative to each other to change an angle formed by the objective optical axes of the light-receiving systems.

According to the embodiment, the stereo angle can be suitably changed.

DETAILED DESCRIPTION

Figure 1:
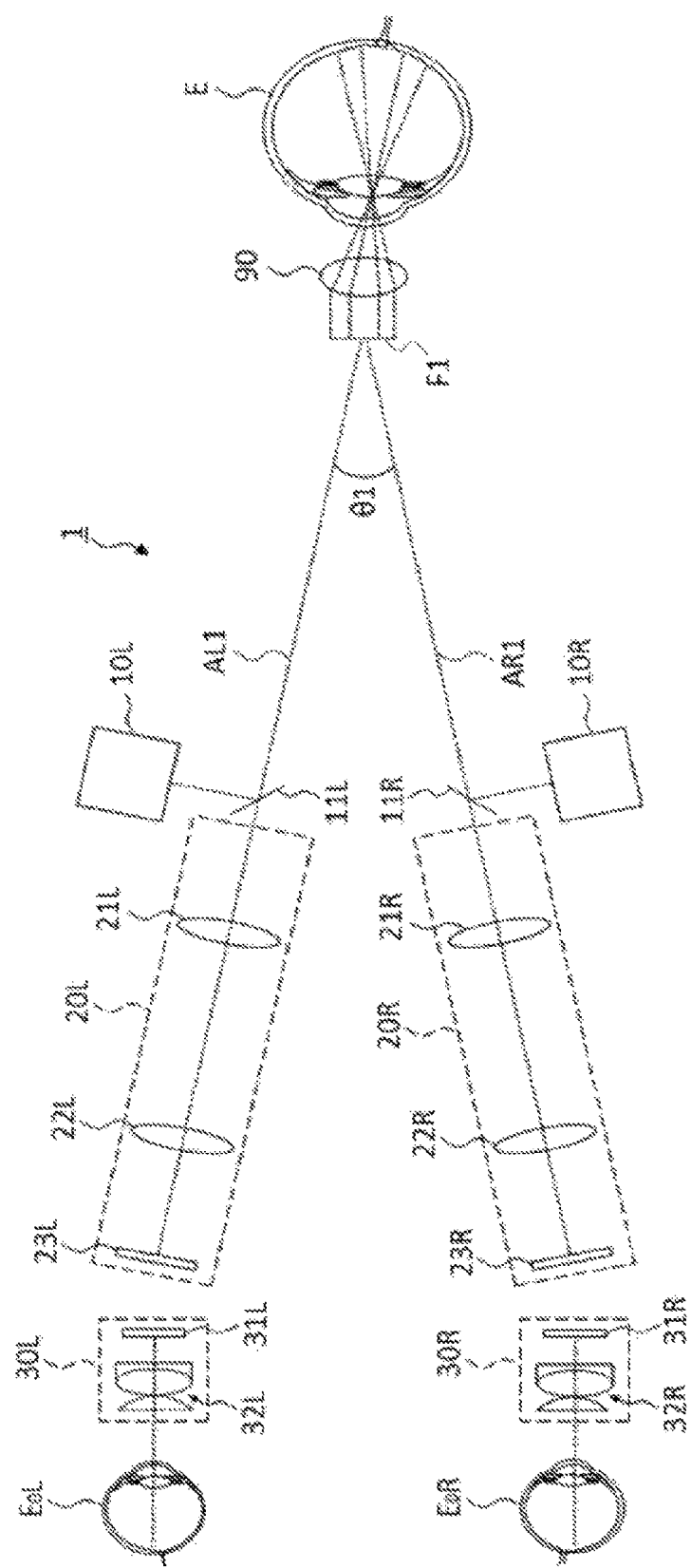
FIG. 1 is a schematic diagram illustrating an example of the configuration of an ophthalmic microscope according to an embodiment.

Referring now to the drawings, a description is given of an ophthalmic microscope according to embodiments. The known technologies and the disclosure of the references cited in this specification may be incorporated herein by reference.

The ophthalmic microscope is used for treatment and surgery in the ophthalmic field to observe (and photograph) an enlarged image of the subject's eye. Any portion of the subject's eye may be an object to be observed. Examples of the observation object include the cornea, the corner, the vitreous body, the crystalline lens, and the ciliary body in the anterior segment of the eye, and the retina, the choroid, and the vitreous body in the posterior segment. The observation object may also be a peripheral portion of the eye, such as the eyelid and the eye socket.

<Configuration>

Figure 2:
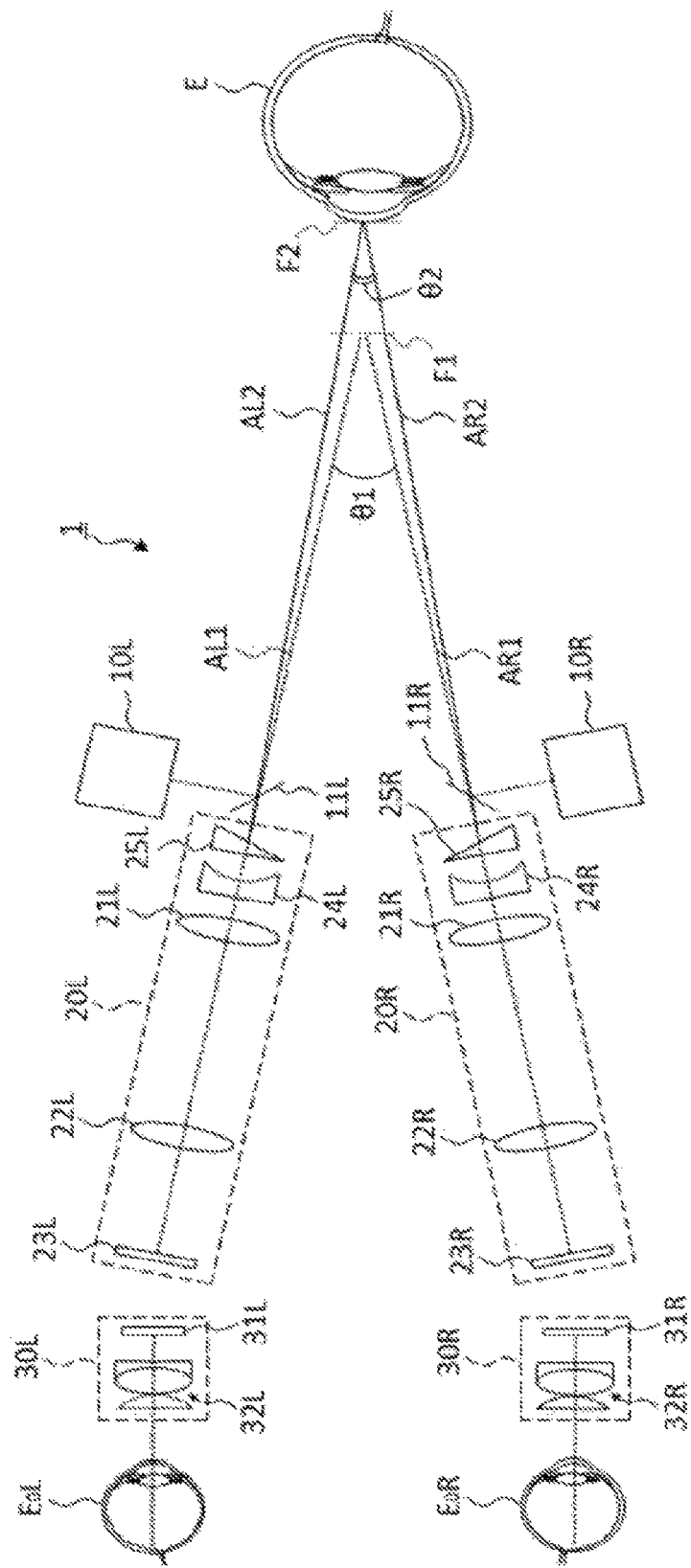
FIG. 2 is a schematic diagram illustrating an example of the configuration of the ophthalmic microscope of the embodiment.
Figure 3:
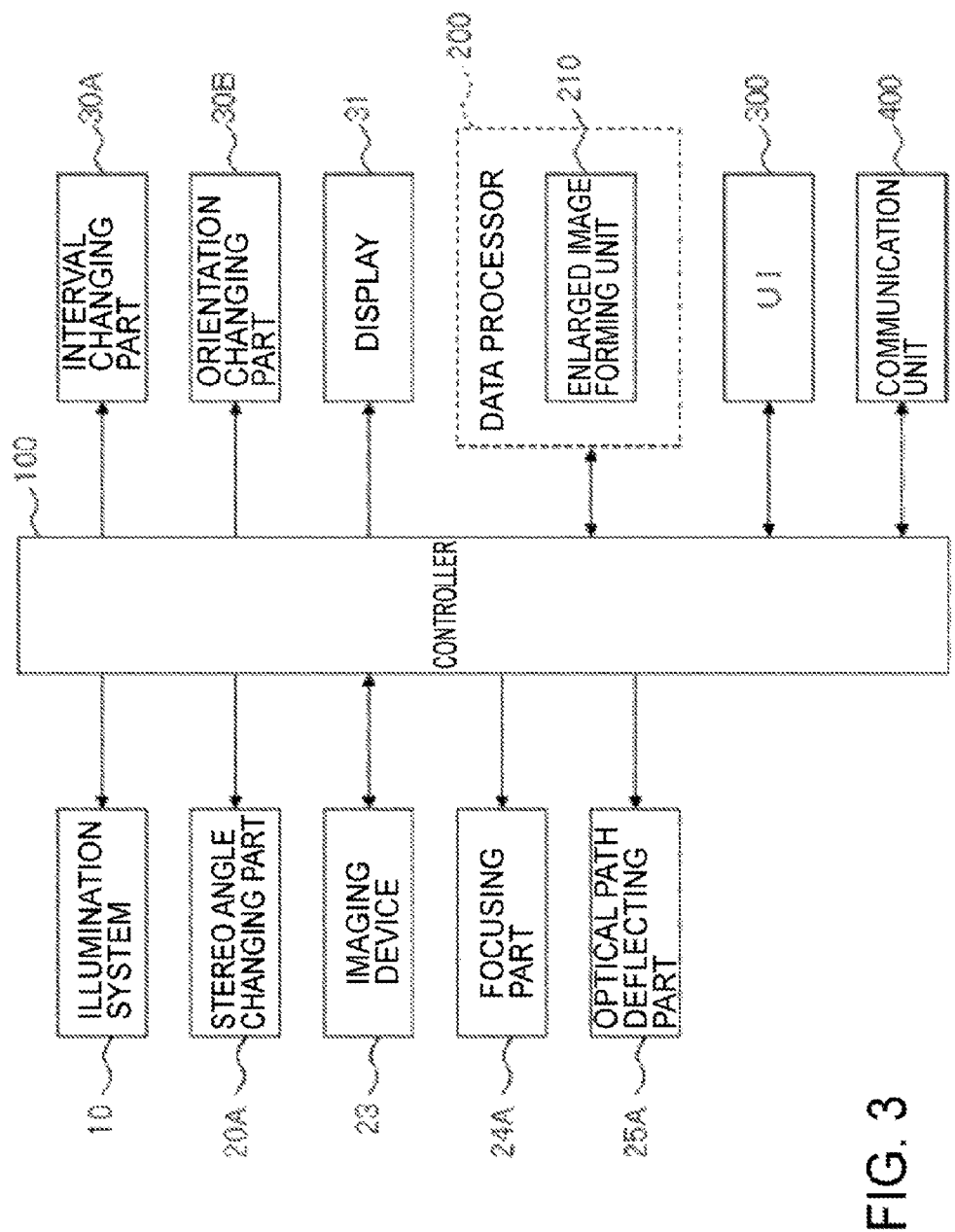
FIG. 3 is a schematic diagram illustrating an example of the configuration of the ophthalmic microscope of the embodiment.

FIGS. 1 to 3 illustrate the configuration of an ophthalmic microscope 1 according to an embodiment. FIGS. 1 and 2 illustrate the configuration of the optical system. FIG. 1 illustrates the optical system when the posterior segment of the eye is being observed. FIG. 2 illustrates the optical system when the anterior segment is being observed. FIG. 3 illustrates the configuration of the processing system.

The ophthalmic microscope 1 includes illumination systems 10 (10L, 10R), light-receiving systems 20 (20L, 20R), and ocular systems 30 (30L, 30R). During the observation of the posterior segment of the eye (the retina, etc.), a front lens

90 is placed immediately before the subject's eye E. Incidentally, instead of the non-contact front lens 90 as illustrated in FIG. 1, a contact lens or the like can be used. Besides, a contact mirror (triple mirror, etc.) or the like can be used for viewing the corner.

(Illumination Systems 10)

The illumination systems 10 illuminate the subject's eyes E with illumination light. Although not illustrated, the illumination systems 10 each include a light source that emits illumination light, an aperture that defines the illumination field, a lens system, and the like. The illumination systems 10 may have the same configuration as that of conventional ophthalmic devices (e.g., slit lamp microscope, fundus camera, refractometer, etc.).

The illumination systems 10L and 10R of the embodiment are configured to be coaxial with the light-receiving systems 20L and 20R, respectively. Specifically, a beam splitter 11L formed of, for example, a half mirror is obliquely arranged with respect to the left light-receiving system 20L for obtaining an image to be presented to the viewer's left eye $E_0L$. The beam splitter 11L couples the optical path of the left illumination system 10L with the optical path of the left light-receiving system 20L. The illumination light output from the left illumination system 10L is reflected by the beam splitter 11L, and illuminates the subject's eye E in coaxial with the left light-receiving system 20L. Similarly, a beam splitter 11R for coupling the optical path of the right illumination system 10R with the optical path of the right light-receiving system 20R is obliquely arranged with respect to the right light-receiving system 20R for obtaining an image to be presented to the viewer's right eye $E_0R$.

The position of the illumination light can be varied with respect to the optical axis of the light-receiving system 20L (20R). This can be implemented by, for example, providing a means for changing the irradiation position of the illumination light to the beam splitter 11L (11R), as in a conventional ophthalmic surgical microscope.

Although, in this example, the beam splitter 11L (11R) is located between the subject's eye E and an objective lens 21L (21R), the optical path of illumination light may be coupled with the light-receiving system 20L (20R) at any position in the light-receiving system 20L (20R).

(Light-Receiving Systems 20)

In this embodiment, there is provided a pair of the left and right light-receiving systems 20L and 20R. The left light-receiving system 20L is configured to obtain an image to be presented to the viewer's left eye $E_0L$. The right light-receiving system 20R is configured to obtain an image to be presented to the right eye $E_0R$. The left light-receiving system 20L and the right light-receiving system 20R have the same configuration. The left light-receiving system 20L (the right light-receiving system 20R) includes the objective lens 21L (21R), an imaging lens 22L (22R), and an imaging device 23L (23R).

The imaging lens 22L (22R) may be dispensed with. When the imaging lens 22L (22R) is provided as in this embodiment, a path between the objective lens 21L (21R) and the imaging lens 22L (22R) may be made an afocal optical path (parallel optical path). Thus, it is facilitated to arrange an optical element such as a filter, and to couple with an optical path from another optical system by an optical path coupling member (i.e., the flexibility and scalability of the optical structure are improved).

Sign AL1 indicates the optical axis (objective optical axis) of the objective lens 21L of the left light-receiving system 20L. Sign AR1 indicates the optical axis (objective optical axis) of the objective lens 21R of the right light-receiving system 20R. The angle $\theta 1$ formed by the left optical axis AL1 and the right optical axis AR1 is a stereo angle in the state of FIG. 1. The imaging device 23L (23R) may be an area sensor such as, for example, a charge-coupled device (CCD) image sensor or a complementary metal-oxide semiconductor (CMOS) image sensor.

Described above is the configuration of the light-receiving systems 20 for observing the posterior segment (fundus) of the subject's eye (FIG. 1). On the other hand, to observe the anterior eye segment, as illustrated in FIG. 2, a focus lens 24L (24R) and a wedge prism 25L (25R) are each arranged in a position on the subject's eye E side with respect to the objective lens 21L (21R). The focus lens 24L (24R) of this example is a concave lens, and acts to increase the focal length of the objective lens 21L (21R). The wedge prism 25L (25R) deflects the optical path (objective optical axis AL1 (AR1)) of the left light-receiving system 20L (the right light-receiving system 20R) to the outside by a predetermined angle (indicated by signs AL2 and AR2). In this manner, the focus lens 24L and the wedge prism 25L are placed in the left light-receiving system 20L. Similarly, the focus lens 24R and the wedge prism 25R are placed in the right light-receiving system 20R. Thereby, a focus position F1 for posterior eye segment observation can be switched to a focus position F2 for anterior eye segment observation.

The angle $\theta 2$ formed by the left and right objective optical paths (objective optical axes) AL2 and AR2 deflected by placing the focus lenses 24L and 24R as well as the wedge prisms 25L and 25R indicates a stereo angle in the state shown in FIG. 2. In other words, by the placement of the focus lenses 24L and 24R as well as the wedge prisms 25L and 25R, the stereo angle of a pair of the light-receiving systems 20L and 20R is switched from the stereo angle $\theta 1$ for the posterior eye segment observation to stereo angle $\theta 2$ for the anterior eye segment observation.

A convex lens can be used as the focus lens. In this case, the focus lens is placed in the optical path at the time of the observation of the posterior segment of the subject's eye, and is retracted from the optical path at the time of the observation of the anterior segment. Instead of the insertion/retraction of the focusing lens to change the focal length, for example, a focus lens that is movable in the optical axis direction may be provided to continuously or stepwisely change the focal length.

In the example of FIG. 2, while the base direction of the wedge prism 25L (25R) is the outside (i.e., base-out arrangement), a wedge prism for base-in arrangement may be used. In this case, the wedge prism is placed on the optical path at the time of the observation of the posterior segment of the subject's eye, and is retracted from the optical path at the time of the observation of the anterior segment. Instead of the insertion/retraction of the wedge prisms to change the direction of the optical path, a prism having a variable prism amount (and prism direction) may be provided to continuously or stepwisely change the direction of the optical path.

(Ocular Systems 30)

In this embodiment, there is provided a pair of the left and right ocular systems 30L and 30R. The left ocular system 30L is configured to present an image of the subject's eye E obtained by the left light-receiving system 20L to the viewer's left eye $E_0L$. The right ocular system 30R is configured to present an image of the subject's eye E obtained by the right light-receiving system 20R to the right eye $E_0R$. The left ocular system 30L and the right ocular system 30R have the same configuration. The left ocular system 30L (the right ocular system 30R) includes a display 31L (31R), and an ocular lens system 32L (32R).

The display 31L (31R) is a flat panel display such as, for example, liquid crystal display (LCD). The display 31L (31R) has a display surface in a size of, for example, 7 inches or less (diagonal length). The left and right ocular systems 30L and 30R are provided with a display device having a screen the size of which is restricted by the viewer's eye width (pupillary distance, etc.), the size of the device, the design of the device (the arrangement of the optical systems and mechanisms), and the like. That is, such restriction conditions and the width of the field of view are in a trade-off relationship. From this point of view, the maximum screen size of the displays 31L and 31R is presumably about 7 inches. Incidentally, by devising the configuration of the ocular lens systems 32L and 32R and the arrangement of mechanisms, the displays 31L and 31R having a screen larger than 7 inches or a smaller screen can be used.

As described below, the distance between the left ocular system 30L and the right ocular system 30R can be changed. Accordingly, it is possible to adjust the distance between the left ocular system 30L and the right ocular system 30R according to the eye width of the viewer. Besides, the relative orientations of the left ocular system 30L and the right ocular system 30R can also be changed. In other words, it is possible to change the angle between the optical axes of the left and right ocular systems 30L and 30R. With this, it is possible to induce binocular convergence of the eyes $E_oL$ and $E_oR$, thereby supporting the stereoscopic view of the viewer.

(Controller 100)

Figure 5A:
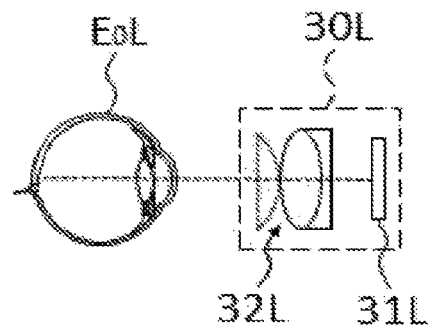
FIG. 5A is a schematic diagram illustrating an example of the action of the ophthalmic microscope of the embodiment.
Figure 5A:
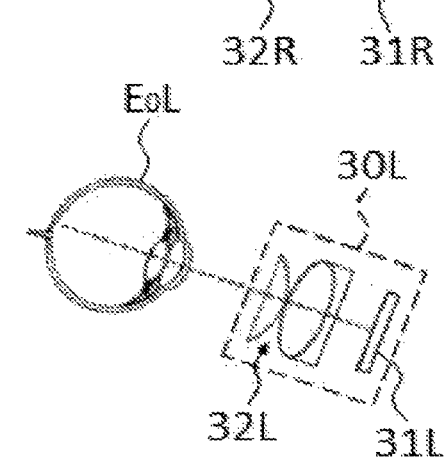

A controller 100 controls each part of the ophthalmic microscope 1 (see FIG. 5). Examples of the control for the illumination systems 10 include turning on and off the light source, light amount adjustment, diaphragm adjustment, and, if slit lighting is available, slit width adjustment. Examples of the control for the imaging device 23 include exposure adjustment, gain adjustment, and shooting rate adjustment.

The controller 100 displays various types of information on the display 31. For example, the controller 100 displays an image captured by the imaging device 23L (or an image obtained by processing it) on the display 31L as well as displaying an image captured by the imaging device 23R (or an image obtained by processing it) on the display 31R. At this time, the controller 100 can change the orientation of the image captured by the imaging device 23L (23R) to display it on the display 31L (31R). For example, as in the embodiment, when the light-receiving system is not provided with an inverter that converts an inverted image into an erect image, the controller 100 can invert the image captured by the imaging device 23L (23R) to thereby display an erect image on the display 31L (31R). Further, if the ocular lens system 32L (32R) is configured to reverse an image displayed on the display 31L (31R) to present it to the left eye $E_oL$ (the right eye $E_oR$), the controller 100 controls the display 31L (31R) to display an inverted image thereon. This configuration eliminates the need of the inverter, resulting in a reduction in the number of members in the optical system. Thus, the cost-cutting and downsizing of the device can be achieved.

Further, the controller 100 controls various mechanisms. Examples of the mechanisms include a stereo angle changing part 20A, a focusing part 24A, an optical path deflecting part 25A, an interval changing part 30A, and an orientation changing part 30B.

The stereo angle changing part 20A rotates the left light-receiving system 20L and the right light-receiving system 20R relative to each other. That is, the stereo angle changing part 20A causes relative movement of the left light-receiving system 20L and the right light-receiving system 20R to change the angle formed by their objective optical axes (e.g., AL1 and AR1). By this relative movement, for example, the left light-receiving system 20L and the right light-receiving system 20R are moved by the same angle to the opposite rotation directions. In this movement mode, the direction of the bisector of the angle formed by the objective optical axes (e.g., AL1 and AR1) is constant. Note that it is also possible to perform the relative movement such that the direction of the bisector is allowed to vary.

Figure 4:
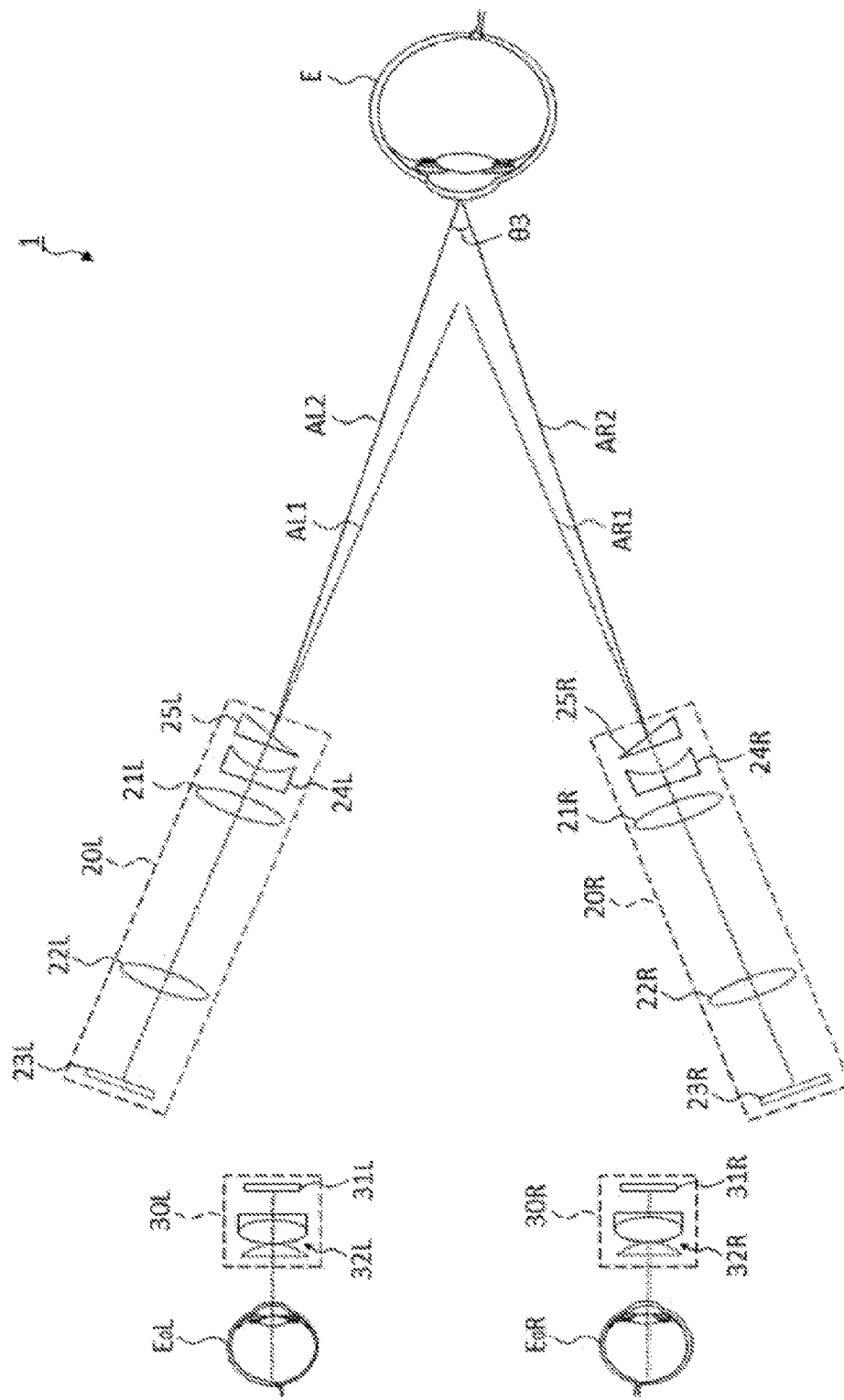
FIG. 4 is a schematic diagram illustrating an example of the action of the ophthalmic microscope of the embodiment.

FIG. 4 illustrates an example of the stereo angle which has been increased from the state illustrated in FIG. 2 by controlling the stereo angle changing part 20A. A stereo angle $θ3$ illustrated in FIG. 4 is greater than a stereo angle $θ2$ illustrated in FIG. 2. Incidentally, when the stereo angle changing part 20A changes the stereo angle, the relative positions (distance, relative orientation) of the left and right ocular systems 30L and 30R do not change. Besides, in response to a change in the stereo angle, the control can be performed to adjust the distance between the left and right light-receiving systems 20L and 20R with respect to the eye E, or to change the focal length of the left and right light-receiving systems 20L and 20R, to thereby prevent a shift in the focus position.

The focusing part 24A is configured to insert/retract the left and right focus lenses 24L and 24R into/from the optical path. The focusing part 24A may be configured to simultaneously insert/retract the left and right focus lenses 24L and 24R. For another example, the focusing part 24A may be configured to move the left and right focus lenses 24L and 24R (at the same time) in the optical axis direction to change the focus position. Further, the focusing part 24A may be configured to change the refractive power of the left and right focus lenses 24L and 24R (at the same time) to change the focal length.

The optical path deflecting part 25A is configured to insert/retract the left and right wedge prisms 25L and 25R into/from the optical path. The optical path deflecting part 25A may be configured to simultaneously insert/retract the left and right wedge prisms 25L and 25R. For another example, the optical path deflecting part 25A may be configured to change the prism amount (and the prism direction) of the left and right wedge prisms 25L and 25R (at the same time) to change the orientation of the optical paths of the left and right light-receiving systems 20L and 20R.

The interval changing part 30A changes the distance between the left and right ocular systems 30L and 30R. The interval changing part 30A may be configured to move the left and right ocular systems 30L and 30R relative to each other without changing the relative orientation of their optical axes.

The orientation changing part 30B changes the relative orientations of the left and right ocular systems 30L and 30R. The orientation changing part 30B is configured to move the left and right ocular systems 30L and 30R relative to each other to change the angle formed by their optical axes. By this relative movement, for example, the left ocular system 30L and the right ocular system 30R are moved by the same angle to the opposite rotation directions. In this movement mode, the direction of the bisector of the angle formed by the optical axes is constant. Note that it is also possible to perform the relative movement such that the direction of the bisector is allowed to vary.

Figure 5B:
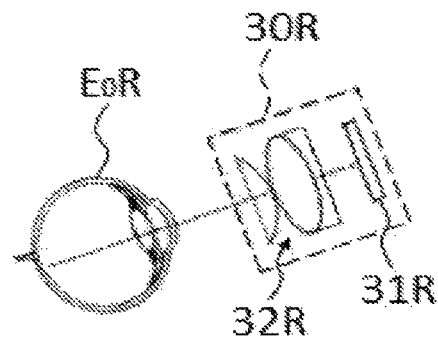
FIG. 5B is a schematic diagram illustrating an example of the action of the ophthalmic microscope of the embodiment.

FIG. 5A illustrates the relative orientations of the left and right ocular systems 30L and 30R in the state illustrated in FIG. 1 or 2. In this state, the left and right ocular systems 30L and 30R are arranged such that their optical axes are parallel to each other (parallel vision state). FIG. 5B illustrates an example of the relative orientations of the left and right ocular systems 30L and 30R which has been changed from the state illustrated in FIG. 5A by controlling the orientation changing part 30B. In the state illustrated in FIG. 5B, the optical axes of the left and right ocular systems 30L and 30R are not parallel to each other (inner vision state). Note that, by controlling the orientation changing part 30B, the angle formed by the optical axes of the left and right ocular systems 30L and 30R can be changed in any fashion (e.g., changed continuously or stepwisely).

(Data Processor 200)

A data processor 200 performs various types of data processing. The data processing includes image forming, image processing, and the like. The data processor 200 may perform processing related to the analysis of images, examination results, and measurement results, and processing related to information about the subject (electronic medical record information, etc.). The data processor 200 includes an enlarged image forming unit 210.

The enlarged image forming unit 210 expands an image captured by the imaging device 23. This process is so-called digital zooming, and includes a process of cutting out a part of the image captured by the imaging device 23, and a process of creating an enlarged image of the part. The area in the image to be cut out is set by the viewer or the controller 100. The enlarged image forming unit 210 performs the same process on an image (left image) captured by the imaging device 23L of the left light-receiving system 20L, and an image (right image) captured by the imaging device 23R of the right light-receiving system 20R. Thereby, the image is presented at the same magnification to the left eye $E_OL$ and the right eye $E_OR$ of the viewer.

Incidentally, in addition to or instead of the digital zoom function, so-called optical zoom function may be provided. The optical zoom function is realized by providing a variable magnification lens (variable magnification lens system) to each of the left and right light-receiving systems 20L and 20R. As a specific example, the variable magnification lens may be (selectively) inserted into/retracted from the optical path, or the variable magnification lens may be moved along the optical axis direction. The controller 100 performs controls related to the optical zoom function.

(User Interface 300)

A user interface (UI) 300 has a function for exchanging information between the viewer or the like and the ophthalmic microscope 1. The user interface 300 includes a display device and an operation device (input device). The display device may include the display 31 and/or another display. The operation device includes various hardware keys and/or software keys. At least part of the operation device may be integrated with at least part of the display device. For example, a touch panel display offers the integrated functions of the display device and the operation device.

(Communication Unit 400)

A communication unit 400 is configured to transmit information to another device and receive information sent from another device. The communication unit 400 may include a communications device conforming to a predetermined network (LAN, the Internet, etc.). For example, the communication unit 400 acquires information from an electronic medical record database and a medical image database via LAN provided in a medical institution. If there is provided an external monitor, the communication unit 400 can transmit images acquired by the ophthalmic microscope 1 to the external monitor substantially in real-time.

<Operations and Effects>

Described below are the operations and effects of the embodiment.

According to this embodiment, the ophthalmic microscope includes illumination systems (10), a pair of light-receiving systems (20L, 20R), and a first mechanism (the stereo angle changing part 20A). The illumination systems are configured to irradiate a subject's eye with illumination light. Each of the light-receiving systems includes a first objective lens (21L, 21R) and a first imaging device (23L, 23R). The objective optical axes (AL1, AR1) of the light-receiving systems are not parallel to each other. Further, the light-receiving systems are each configured to guide return light of the illumination light irradiated to the subject's eye and returning therefrom to the first imaging device through the first objective lens. The first mechanism is configured to move the light-receiving systems relative to each other to change an angle formed by the objective optical axes of the light-receiving systems.

The configuration to move the light-receiving systems relative to each other to change an angle (stereo angle) formed by their objective optical axes can be realized by that the light-receiving systems each have an independent objective lens. Here, the relative movement of the light-receiving systems is, for example, rotation about the focus point of each of the light-receiving systems, or rotation about any preset point. In this case, control can be additionally performed to perform parallel translation of the light-receiving systems such that the focus point does not change before and after the relative movement. On the other hand, in the conventional configuration in which a pair of light-receiving systems shares a common objective lens, the stereo angle cannot be freely changed.

With the ophthalmic microscope, the stereo angle can be freely changed with a simple structure. In addition, the changeable range of the stereo angle can be increased. Typically, with this configuration, a large stereo angle can be realized, and it is possible to obtain an observation image having a three-dimensional appearance. In particular, by applying a sufficiently large stereo angle during an observation at high magnification, an observation image having a three-dimensional appearance can be achieved. Further, fine adjustment of the stereo angle can be facilitated. For example, if the illumination light or the return light is blocked by the iris during fundus observation, the stereo angle can be reduced depending on the pupil size of the subject's eye.

Further, the conventional mechanism for changing the stereo angle using a prism is very large, which necessitates an increase in the size of the ophthalmic microscope. On the other hand, the ophthalmic microscope of the embodiment is provided with only the first mechanism for moving the light-receiving systems, which does not increase the size of the device differently from the conventional ophthalmic microscope. Further, according to the embodiment, the light-receiving systems each include an objective lens, and an objective lens having a large diameter, which is shared by both the light-receiving systems, is not used. Thus, the flexibility of optical design and mechanical design can be improved. In addition, the downsizing of the device can be achieved.

In the embodiment, there may be provided a first controller (the controller 100) configured to display an image on the display based on output from the imaging device of at least one of the light-receiving systems. The display may include a display device provided to the ophthalmic microscope or a display device provided outside of the ophthalmic microscope.

With this configuration, an image(s) obtained by the light-receiving systems can be presented. In the case of presenting images obtained by both of the light-receiving systems, the images may be displayed so that they can be viewed in stereoscopic vision.

As an example in which at least part of the display is provided to the ophthalmic microscope, there may be provided a pair of ocular units (the ocular systems 30L and 30R). Each of the ocular units include a display (the display 31L, 31R), and one or more lenses (the ocular lens system 32L, 32R) placed on the display surface side of the display. The first controller displays an image based on output from the first imaging device (23L) of one of the light-receiving systems (20L) on the display (31L) of one of the ocular units (30L). Similarly, the first controller displays an image based on output from the first imaging device (23R) of the other of the light-receiving systems (20R) on the display (31R) of the other of the ocular units (30R).

With this configuration, the viewer can observe a pair of images captured by the light-receiving systems as if observing optical images through a common binocular eyepiece. By employing such a configuration, it is possible to realize an exit pupil diameter which is sufficiently large as compared to the conventional microscope, thereby improving visibility and relieving fatigue.

In the embodiment, there may be provided a second mechanism (the interval changing part 30A) configured to change the distance between the ocular units.

With this configuration, the distance between the ocular units can be adjusted according to the viewer's eye width (pupillary distance, etc.). Thus, binocular observation can be performed comfortably.

In the embodiment, there may be provided a third mechanism (the orientation changing part 30B) configured to change the relative orientations of the ocular units.

With this configuration, a state where the optical axes of the ocular units are arranged in parallel (parallel view) or a state where the optical axes are not parallel to each other (inside view) can be freely selected by preference, etc. of the viewer. Moreover, by adjusting the angle formed by the optical axes, it is possible to induce binocular convergence of the eyes of the viewer, thereby supporting stereoscopic vision. Further, by combining the convergence adjustment and interpupillary adjustment, the viewer can enjoy stereoscopic vision relatively easily even if he/she has crossed eyes to a certain extent.

In the embodiment, there may be provided an enlarged image forming unit (210) configured to form an enlarged image(s) of the image based on the output from the first imaging device (23L, 23R). The first controller displays the enlarged image(s) formed by the enlarged image forming unit on the display(s) (31L, 31R, etc.)

With this, it is possible to offer an observation of an enlarged view of the subject's eye using so-called digital zoom function. Since the digital zoom function does not require an optical element such as a variable magnification lens or the like, the structure of the optical system can be simplified.

Incidentally, each of the light-receiving systems may include a variable magnification lens. With this, it is possible to offer an observation of an enlarged view of the subject's eye using so-called optical zoom function. Differently from the digital zoom function, the optical zoom function does not impair the image quality.

In the embodiment, there may be provided either or both of the digital zoom function and the optical zoom function. When both of the functions are provided, one of them can be preferentially performed, or they can be performed in combination.

In the embodiment, each of the light-receiving systems may include a lens (the focus lens 24L, 24R) for changing the focus position. Further, there may be provided a fourth mechanism (the focusing part 24A) configured to move these lenses together. For example, the fourth mechanism is configured to insert the lenses together in the optical paths, and to retract them together therefrom. Alternatively, the second mechanism is configured to move the lenses together along the optical axes.

With this, the focus position can easily be changed depending on the portion to be observed. For example, in a conventional structure, it is required to move the microscope itself in the longitudinal direction to shift from anterior eye segment observation to fundus observation. On the other hand, according to this embodiment, the focus position can easily be changed by the insertion/retraction of the lenses or the movement of the lenses.

In the embodiment, each of the light-receiving systems may include a deflecting member (the wedge prism 25L, 25R) for deflecting the optical path. Further, there may be provided a fifth mechanism (the optical path deflecting part 25A) to move these deflecting members together. For example, the fifth mechanism is configured to insert the deflection members together in the optical paths, and to retract them together therefrom.

With this configuration, the focus position can easily be changed depending on the portion to be observed. In particular, by the combination of the configuration with the lens for changing the focus position and the fourth mechanism for moving them together, the focus position can be shifted more suitably.

In the embodiment, there may be provided an optical path coupling member (beam splitter 11L, 11R) configured to couple the optical path of each of the light-receiving systems with the optical path of each of the illumination systems. In other words, the illumination systems and the light-receiving systems can be formed coaxially. Incidentally, an example is described later in which the illumination systems and the light-receiving systems are arranged in a non-coaxial manner.

In the embodiment, there may be provided a light-receiving system different from the light-receiving systems (main light-receiving system). In particular, there may be provided a pair of light-receiving systems different from the main light-receiving systems. As with the main light-receiving systems, the "other light-receiving systems" each include an objective lens and an imaging device, and their objective optical axes are not parallel to each other. The other light-receiving systems are each configured to guide the illumination light irradiated to the subject's eye and returning therefrom to the imaging device through the objective lens. The light-receiving systems are used as, for example, an assistant's microscope. For example, in surgery, the surgeon uses the main light-receiving systems, while assistants use the assistant's microscope. A pair of images acquired by the assistant's microscope is presented, for example, via another pair of ocular units having the same structure as the ocular units. In addition, any structure and features regarding the main light-receiving systems can be applied in a similar manner to the assistant's microscope.

<Modifications>

The embodiments described above are mere examples for implementing the present invention, and therefore susceptible to several modifications and variations (omission, substitution, addition, etc.), all coming within the scope of the invention.

(Modification 1)

In the above embodiment, the focus lenses 24L and 24R as well as the wedge prisms 25L and 25R are retracted from the optical path at the time of fundus observation, and inserted into the optical path at the time of anterior eye segment observation. Such operations can be automated. In the embodiment, an auxiliary optical member is used to change the portion of the subject's eye to be observed. For example, at the time of fundus observation, the front lens 90 is placed in the optical path. Meanwhile, at the time of anterior eye segment observation, it is retracted from the optical path.

According to this modification, the ophthalmic microscope changes the state of the focus lenses 24L and 24R depending on the state of the auxiliary optical member (i.e., the selection of the portion to be observed). That is, in response to a change in the portion to be observed by the auxiliary optical member, the controller 100 controls the fourth mechanism for moving the focus lenses 24L and 24R together. Similarly, in response to a change in the portion to be observed by the auxiliary optical member, the controller 100 controls the fifth mechanism for moving the wedge prisms 25L and 25R together.

Described below are specific examples. When the front lens 90 is retracted from the optical path, the controller 100 controls the focusing part 24A and the optical path deflecting part 25A to insert the focus lenses 24L and 24R as well as the wedge prisms 25L and 25R in the optical path. On the other hand, when the front lens 90 is inserted into the optical path, the controller 100 controls the focusing part 24A and the optical path deflecting part 25A to retract the focus lenses 24L and 24R as well as the wedge prisms 25L and 25R therefrom.

The ophthalmic microscope of this modification may have a structure for generating information that indicates the state of the auxiliary optical member (e.g., whether the front lens 90 is placed in the optical path). For example, the arrangement of arms that hold the front lens 90 can be detected by using a sensor such as a micro switch. Alternatively, if the insertion/retraction of the front lens 90 is performed based on a signal from the controller 100, the current state of the front lens 90 can be acquired by referring to the history of the control.

For another example, it is possible to determine whether the front lens 90 is located in the optical path based on an image(s) captured by the imaging device(s) 23L and/or 23R, and the current state of the focus lenses 24L and 24R as well as the wedge prisms 25L and 25R. For example, the data processor 200 analyzes an image obtained in the state where the focus lens 24L and the like are located in the optical path to calculate an amount indicating a blur of the image. If the blur amount is equal to or above a threshold, the front lens 90 is determined to be located in the optical path. On the other hand, when the blur amount is less than the threshold, the front lens 90 is determined to have been retracted from the optical path. In the case of analyzing an image obtained when the focus lens 24L and the like have been retracted from the optical path, the state of the front lens 90 can be determined in the same manner.

According to this modification, it is possible to automatically change the state of the lens (the focus lenses 24L and 24R) for changing the focus position, and the state of the deflecting member (the wedge prisms 25L and 25R) for deflecting the optical path according to a change in the portion to be observed. Therefore, the operability can be further improved.

(Modification 2)

Figure 6:
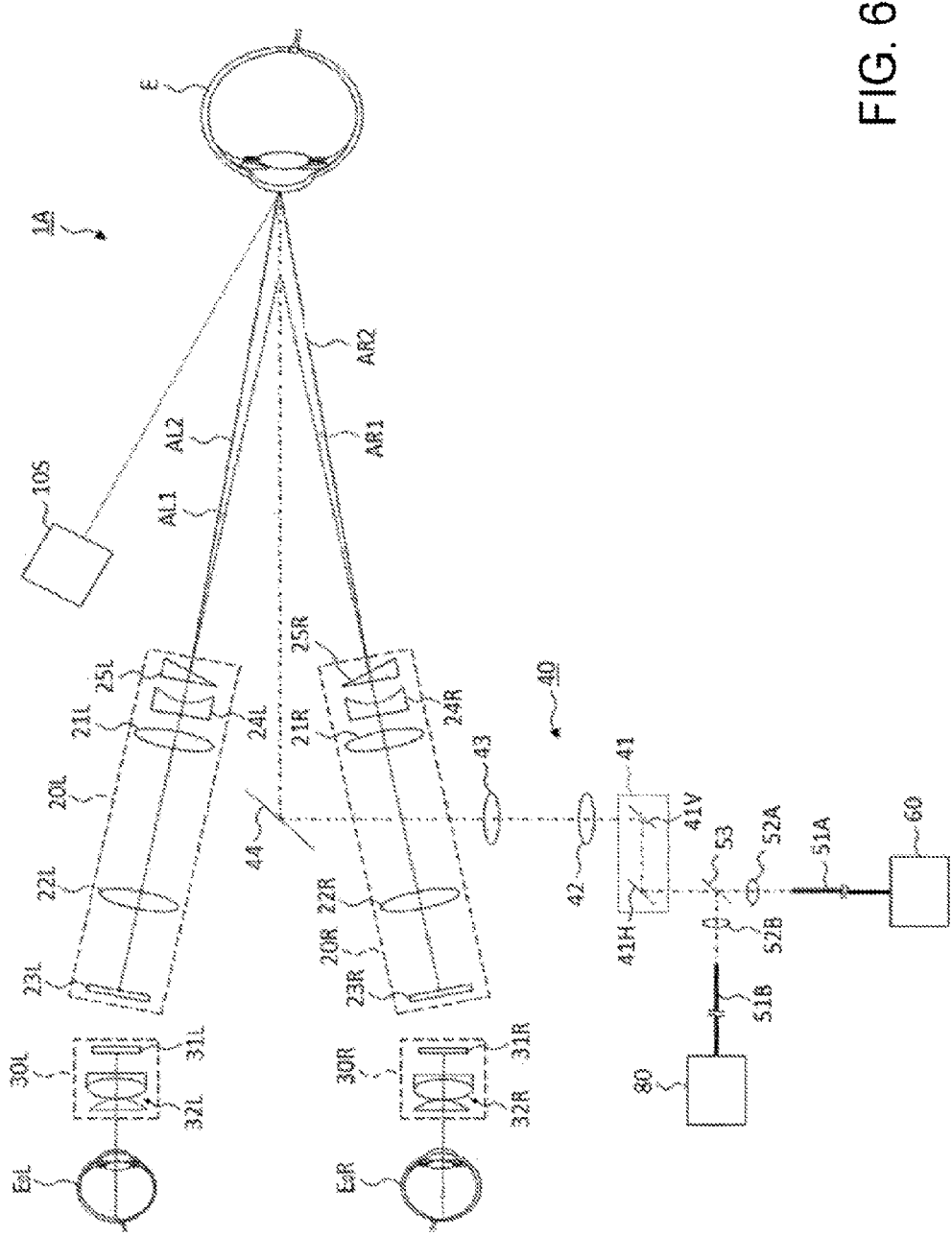
FIG. 6 is a schematic diagram illustrating an example of the configuration of an ophthalmic microscope according to a modification.
Figure 7:
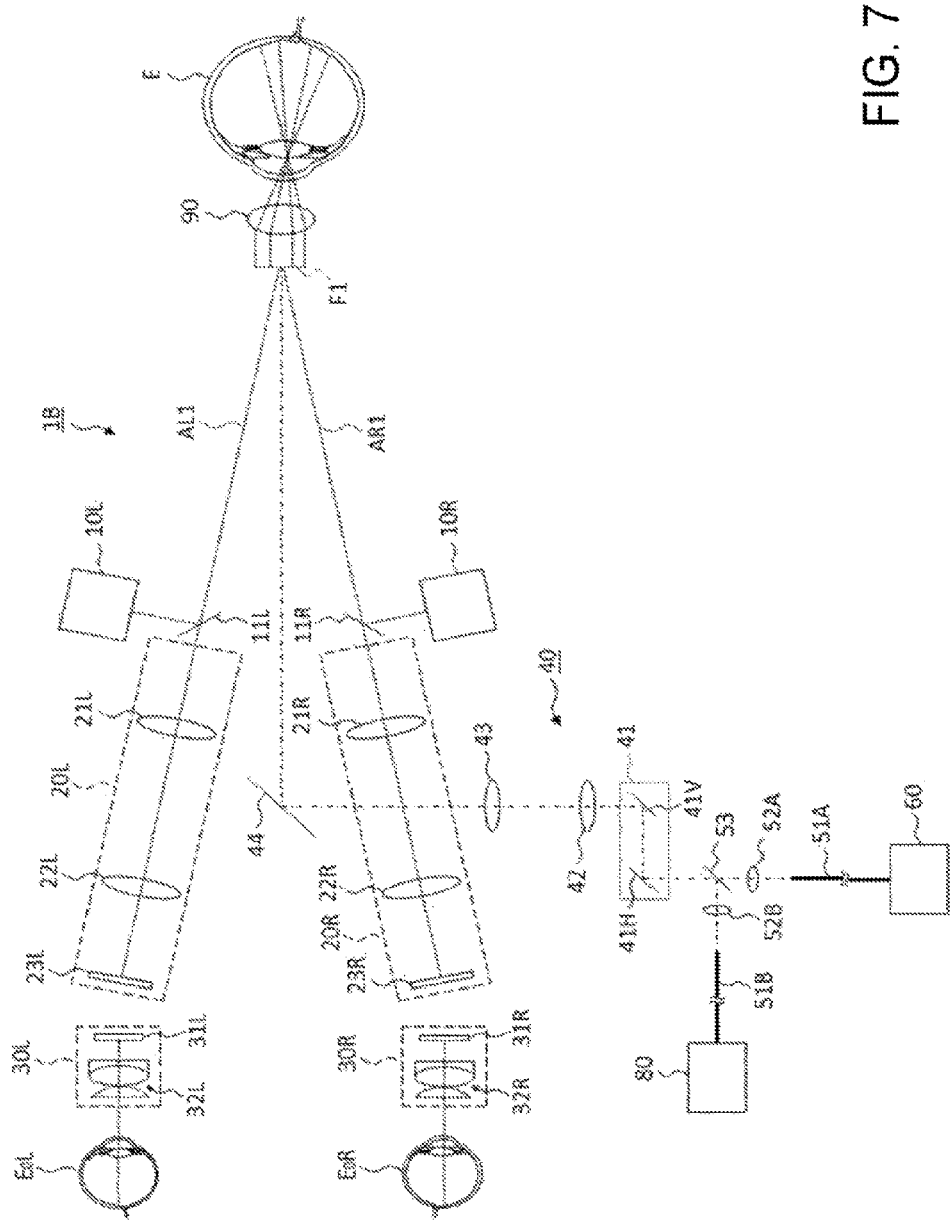
FIG. 7 is a schematic diagram illustrating an example of the configuration of an ophthalmic microscope according to a modification.

The illumination systems (10L and 10R) of the above embodiment are placed coaxially with a pair of the light-receiving systems (20L and 20R). In this modification, illumination systems are arranged in a non-coaxial manner with respect to a pair of light-receiving systems. In other words, the illumination systems are capable of irradiating illumination light from a direction different from the objective optical axes of the light-receiving systems. FIG. 6 illustrates an example of the configuration of the optical system of the modification. An illumination system 10S of an ophthalmic microscope 1A is, for example, capable of irradiating the subject's eye with slit light. As a typical example of the ophthalmic microscope may be cited a slit lamp microscope. In this modification, as in the slit lamp microscope, the relative position between the illumination system 10S and the light-receiving systems 20L and 20R can be changed. In other words, the illumination system 10S as well as the light-receiving systems 20L and 20R are configured to be rotatable about the same axis. Thereby, it is possible to observe a cross section of the cornea and the like illuminated by the slit light from an oblique direction.

The ophthalmic microscope may include either or both of the coaxial illumination systems as described in the above embodiment, and the non-coaxial illumination systems as described in this modification. When provided with both of the illumination systems, for example, the ophthalmic microscope can switch the illumination systems to be used according to a change in the portion to be observed.

(Modification 3)

As well as functioning as a microscope for observing an enlarged view of the eye, the ophthalmic microscope has the function of another ophthalmic device. Examples of the function as another ophthalmic device include optical coherence tomography (OCT), laser treatment, ocular axial length measurement, refractive power measurement, higher-order aberration measurement, and the like. The other ophthalmic device has any configuration capable of examining, measuring and/or imaging the subject's eye by using an optical technique.

FIGS. 7 to 10 illustrate an example of the configuration of an ophthalmic microscope 1B according to this modification. The ophthalmic microscope 1B has OCT function and laser treatment function in addition to the configuration described in the above embodiment. Specifically, the ophthalmic microscope 1B includes an irradiation system 40, an OCT unit 60, and a laser treatment unit 80 in addition to the illumination systems 10, the light-receiving systems 20, and the ocular systems 30 as described above.

The irradiation system 40 irradiates the subject's eye E with illumination light, for realizing the function of "another ophthalmic device" described above, from a direction different than the objective optical axes (AL1 and AR1) of the light-receiving systems 20. The irradiation system 40 of this modification irradiates the subject's eye E with light for OCT (measurement light) and light for laser treatment (aiming light, treatment laser beam).

The irradiation system 40 includes an optical scanner 41, an imaging lens 42, a relay lens 43, and a deflecting mirror 44. The light from the OCT unit 60 and the laser treatment unit 80 is guided to the optical scanner 41.

The light (measurement light) from the OCT unit 60 is guided through an optical fiber 51A, and is emitted from the fiber end face. A collimator lens 52A is located in a position facing the fiber end face. The measurement light collimated by the collimator lens 52A into a parallel light flux is guided to an optical path coupling member 53 that couples the optical path for OCT with the optical path for laser treatment. On the other hand, the light from the laser treatment unit 80 (aiming light, treatment laser beam) is guided through an optical fiber 51B, and is emitted from the fiber end face. A collimator lens 52B is located in a position facing the fiber end face. The measurement light collimated by the collimator lens 52B into a parallel light flux is guided to the optical path coupling member 53.

If the wavelength for OCT is different from the wavelength for laser treatment, a dichroic mirror can be used as the optical path coupling member 53. Typically, a broadband light with a center wavelength of approximately 1050 nm can be used as the light for OCT. Besides, a laser beam with a wavelength of about 635 nm can be used as the light for laser treatment (as the aiming light, for example, any visible light can be used). On the other hand, if both the wavelengths are substantially the same or close to each other, a half mirror can be used as the optical path coupling member 53. For another example, if the timing of performing OCT is different from the timing of performing laser treatment, an optical path switching member such as a quick return mirror can be used as the optical path coupling member 53. In the example illustrated in FIG. 7, the measurement light from the OCT unit 60 transmits through the optical path coupling member 53 and enters the optical scanner 41. The light from the laser treatment unit 80 is reflected by the optical path coupling member 53 and enters the optical scanner 41.

The optical scanner 41 is a two-dimensional optical scanner, and includes an x scanner 41H configured to deflect the light in the horizontal direction (x direction), and a y scanner 41V configured to deflect the light in the vertical direction (y direction). The x scanner 41H and the y scanner 41V may each be an optical scanner of any form, and, for example, galvanometer mirrors are used. The optical scanner 41 is located in, for example, the exit pupil position of each of the collimator lenses 52A and 52B or the vicinity thereof. In addition, the optical scanner 41 is located in, for example, the entrance pupil position of the imaging lens 42 or the vicinity thereof.

When two one-dimensional optical scanners are combined into a two-dimensional optical scanner as in this example, the two one-dimensional optical scanners are spaced apart by a predetermined distance (e.g., about 10 mm). Therefore, for example, any one of the one-dimensional optical scanners can be placed in the exit pupil position and/or the entrance pupil position.

The imaging lens 42 once forms an image of the parallel light flux (measurement light, aiming light, treatment laser beam) having passed through the optical scanner 41. Further, to form an image of the light again at the subject's eye E (more specifically, at a portion to be observed such as the fundus and the cornea), the light is relayed by the relay lens 43, and is reflected toward the subject's eye E by the deflecting mirror 44.

The position of the deflecting mirror 44 is determined in advance such that the light that has been guided by the irradiation system 40 is irradiated, to the subject's eye E, from a direction different than the objective optical axes (AL1 and AR1, and AL2 and AR2) of the light-receiving systems 20. In this example, the deflecting mirror 44 is located in a position between the left light-receiving system 20L and the right light-receiving system 20R, the objective optical axes of which are not parallel to each other. One of the factors that allow such an arrangement is an improvement in the flexibility of the optical structure due to the arrangement of the relay lens 43. In addition, for example, it is possible to design the distance between a position conjugate to the optical scanner in the horizontal direction (the x scanner 41H in this example) and the objective lenses 21L and 21R sufficiently small. Thus, the device can be down-sized.

In general, the scannable range (scannable angle) of the optical scanner 41 is limited. The scannable range can be expanded by using the imaging lens 42 (or an imaging lens system) with a variable focal length. Besides, any configuration to increase the scannable range can be employed.

Figure 8:
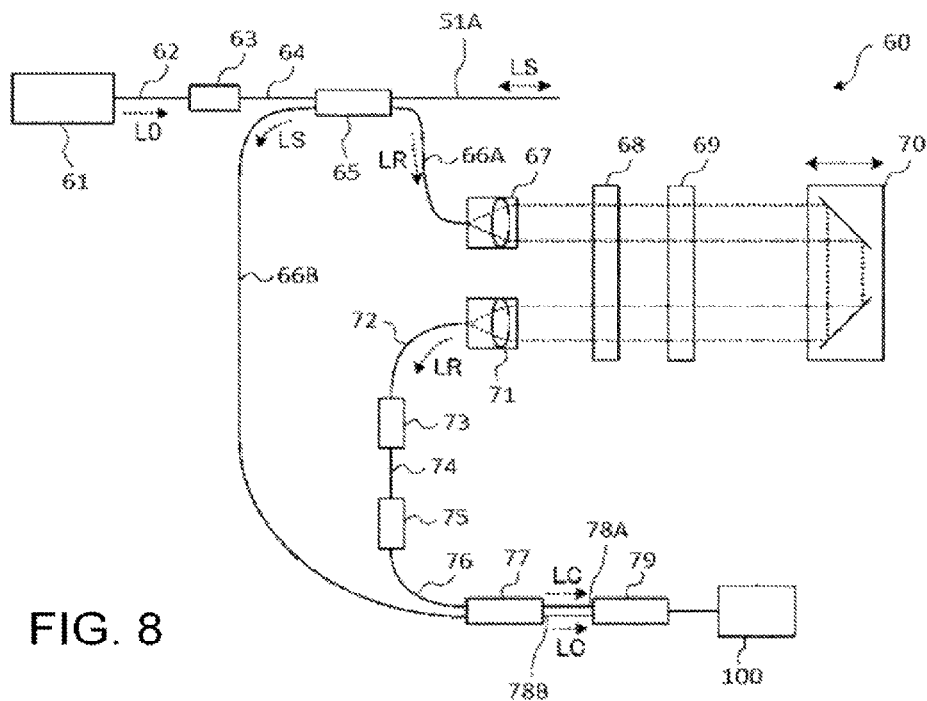
FIG. 8 is a schematic diagram illustrating an example of the configuration of an ophthalmic microscope according to a modification.
Figure 9:
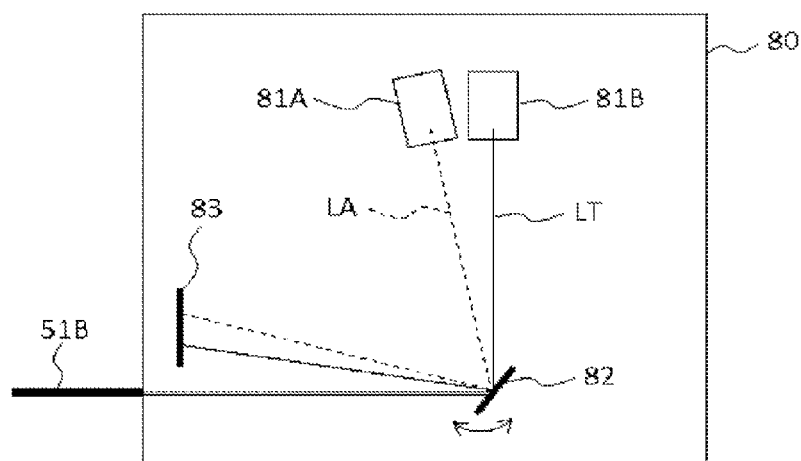
FIG. 9 is a schematic diagram illustrating an example of the configuration of an ophthalmic microscope according to a modification.

The OCT unit 60 includes an interference optical system to perform OCT. FIG. 8 illustrates an example of the configuration of the OCT unit 60. The optical system illustrated in FIG. 8 is an example of a swept-source OCT system. The OCT unit 60 is configured to split the light from a wavelength tunable (wavelength-swept) light source into measurement light and reference light, and make return light of the measurement light having returned from the subject's eye E interfere with the reference light having traveled through a reference optical path to produce interference light. Thereby, the OCT unit 60 detects the interference light. The interference optical system obtains a signal representing the spectrum of the interference light as the detection result (detection signal) of the interference light, and sends it to the controller 100.

Similarly to the general swept-source OCT device, a light source unit 61 includes a wavelength tunable (wavelength-swept) light source capable of varying (sweeping) the wavelength of emission light. The light source unit 61 temporally varies the output wavelength in a range of near infrared wavelengths invisible to the human eye.

Light L0 emitted from the light source unit 61 is guided through an optical fiber 62 to a polarization controller 63, and thereby its polarization state is adjusted. The light L0 is then guided through an optical fiber 64 to a fiber coupler 65, and is split into measurement light LS and reference light LR.

The reference light LR is guided through an optical fiber 66A to a collimator 67 and is collimated into a parallel light flux. The reference light LR then travels through an optical path length correction member 68 and a dispersion compensation member 69, and is guided to a corner cube 70. The optical path length correction member 68 functions as a delay means for matching the optical path length (optical distance) of the reference light LR and the optical path length of the measurement light LS. The dispersion compensation member 69 functions as a dispersion compensation means for matching the dispersion characteristics between the reference light LR and the measurement light LS.

The corner cube 70 reflects the traveling direction of the reference light LR in the reverse direction. The corner cube 70 is movable in a direction along the entrance and exit optical paths of the reference light LR, and thereby the length of the optical path of the reference light LR is changed. Incidentally, it may be sufficient to provide any one of the means for changing the length of the optical path of the measuring beam LS and the means for changing the length of the optical path of the reference light LR.

The reference light LR that has passed through the corner cube 70 travels through the dispersion compensation member 69 and the optical path length correction member 68, and is converted from the parallel light flux into a converging light flux by a collimator 71, and enters an optical fiber 72. The reference light LR is guided to a polarization controller 73, and thereby its polarization state is adjusted. Further, the reference light LR is guided through an optical fiber 74 to an attenuator 75, and the light amount is adjusted under the control of the controller 100. The reference light LR, the amount of which has been adjusted, is then guided through an optical fiber 76 to a fiber coupler 77.

Meanwhile, the measurement light LS generated by the fiber coupler 65 is guided through the optical fiber 51A to be emitted from the end face of the fiber, and is collimated into a parallel light flux by the collimator lens 52A. The measurement light LS collimated into a parallel light flux travels through the optical path coupling member 53, the optical scanner 41, the imaging lens 42, the relay lens 43, and the deflecting mirror 44, and is irradiated onto the subject's eye E. The measurement light LS is reflected and scattered at various depth positions of the subject's eye E. Return light of the measurement light LS returning from the subject's eye E includes reflected light and backscattered light. The measurement light LS is guided to the fiber coupler 65 as traveling the same path as the forward path in the reverse direction, and reaches the fiber coupler 77 via an optical fiber 66B.

The fiber coupler 77 couples (interferes) the measurement light LS incident via the optical fiber 66B with the reference light LR incident via the optical fiber 76 to produce interference light. The fiber coupler 77 divides the interference light at a predetermined branching ratio (e.g., 1:1), and generates a pair of interference light beams LC. The interference light beams LC emitted from the fiber coupler 77 are guided through optical fibers 78A and 78B, respectively, to a detector 79.

The detector 79 may include, for example, a pair of photodetectors for detecting the interference light beams LC, respectively, and a balanced photodiode which outputs a difference in detection results obtained by the photodetectors. The detector 79 sends the detection result (detection signal) to the controller 100.

While swept-source OCT is used in this embodiment, other types of OCT, such as, for example, spectral-domain OCT may also be employed.

The laser treatment unit 80 has a configuration for performing laser treatment. In particular, the laser treatment unit 80 generates light to be irradiated onto the subject's eye E. The laser treatment unit 80 includes an aiming light source 81A, a treatment light source 81B, a galvanometer mirror 82, and a light-shielding plate 83 (see FIG. 9). Incidentally, the laser treatment unit 80 may include a member other than them. For example, an optical element (lens, etc.), which makes the light generated by the laser treatment unit 80 enter the end face of the optical fiber 51B, may be provided just before the position of the optical fiber 51B The aiming light source 81A generates aiming light LA for aiming at a portion subjected to laser treatment. An arbitrary light source is used as the aiming light source 81A. In this embodiment, an aim is set while an image captured of the subject's eye E is being observed. Accordingly, a light source (laser light source, light emitting diode, etc.) that emits light of wavelengths at which the imaging device 23 (23L, 23R) has sensitivity is used as the aiming light source 81A. Incidentally, when aiming operation is carried out by visual observation (that is, by observing an optical image, which is not a captured (or photographed) image), visible light is used as the aiming light LA. The aiming light LA is guided to the galvanometer mirror 82.

The treatment light source 81B emits a treatment laser beam (treatment light LT). The treatment light LT may be either a visible laser beam or an invisible laser beam according to the use. In addition, the treatment light source 81B may be a single laser light source or a plurality of laser light sources configured to emit laser light of different wavelengths. The treatment light LT is guided to the galvanometer mirror 82.

The aiming light LA and the treatment light LT are adapted to reach the same position of the reflecting surface of the galvanometer mirror 82. The treatment light LT and the aiming light LA may sometimes be collectively referred to as "irradiation light". The orientation of (the reflecting surface of) the galvanometer mirror 82 is changed to, at least, the orientation to reflect the irradiation light toward the optical fiber 51B (orientation for irradiation) and the orientation to reflect the irradiation light toward the light-shielding plate 83 (orientation for stop).

When the galvanometer mirror 82 is set to the orientation for stop, the irradiation light reaches the light-shielding plate 83. For example, the light-shielding plate 83 is made of a material and/or in a form to absorb the irradiation light, and has a light-shielding effect.

In this embodiment, each of the aiming light source 81A and the treatment light source 81B generates continuous light. The galvanometer mirror 82 is set to the orientation for irradiation to irradiate the irradiation light to the subject's eye E. Besides, the galvanometer mirror 82 is set to the orientation for stop to stop irradiating the irradiation light to the subject's eye E. In another embodiment, the aiming light source 81A and/or the treatment light source 81B may be configured to be capable of generating light intermittently. That is, the aiming light source 81A and/or the treatment light source 81B may be configured to be able to generate pulse light. The controller 100 performs pulse control for it. In this case, the galvanometer mirror 82 and the light-shielding plate 83 are not needed.

Figure 10:
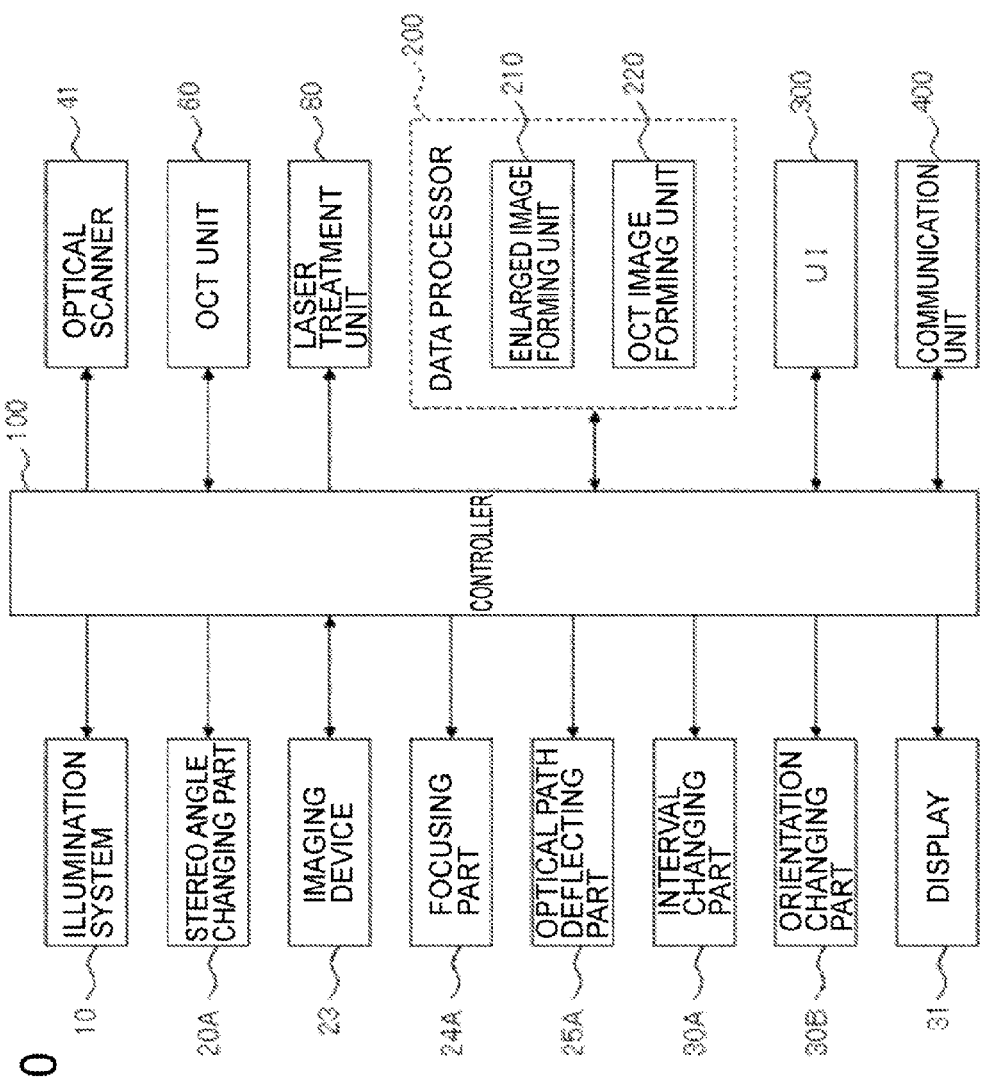
FIG. 10 is a schematic diagram illustrating an example of the configuration of an ophthalmic microscope according to a modification.

FIG. 10 illustrates an example of the configuration of the processing system of the ophthalmic microscope 1B. Described below are the differences from the above embodiment (see FIG. 3). The controller 100 controls the optical scanner 41, the OCT unit 60, and the laser treatment unit 80. The data processor 200 includes an OCT image forming unit 220.

As examples of the control for the optical scanner 41, the controller 100 may control the optical scanner 41 to sequentially deflect the measurement light LS such that the measurement light LS is irradiated to a plurality of positions corresponding to an OCT scan pattern set in advance. In addition, the controller 100 may control the optical scanner 41 to sequentially deflect the aiming light LA and/or the treatment light LT such that the aiming light LA and/or the treatment light LT are/is irradiated to a plurality of positions corresponding to a laser treatment pattern set in advance.

In the OCT unit 60, the controller 100 controls the light source unit 61, the polarization controller 63, the corner cube 70, the polarization controller 73, the attenuator 75, the detector 79, and the like. In the laser treatment unit 80, the controller 100 controls the aiming light source 81A, the treatment light source 81B, the galvanometer mirror 82, and the like.

The OCT image forming unit 220 forms an image of the subject's eye E based on the detection results of the interference light beams LC acquired by the detector 79 of the OCT unit 60. The controller 100 sends detection signals sequentially output from the detector 79 to the OCT image forming unit 220. The OCT image forming unit 220 applies Fourier transform and the like to the spectral distribution based on the detection results acquired by the detector 79 with respect to a series of wavelength scans (for each A-line) to form the reflection intensity profile of each A-line, for example. Further, the OCT image forming unit 220 forms image data by imaging each A-line profile. With this, a B-scan image (sectional image) and volume data (three-dimensional image data) are obtained.

The data processor 200 may have the function of analyzing the image (OCT image) formed by the OCT image forming unit 220. As the analysis may be cited the function of retinal thickness analysis and comparative analysis with the normal eye. The analysis is implemented by using a known application program. Further, the data processor 200 may have the function of analyzing the image captured by the light-receiving systems 20. The data processor 200 may have a combination of the function of analyzing the image captured by the light-receiving systems 20 and the function of analyzing the OCT image.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic microscope, comprising:
an illumination system configured to irradiate a subject's eye with illumination light;
a pair of light-receiving systems each including a first objective lens and a first imaging device, configured to guide return light of the illumination light returning from the subject's eye to the first imaging device through the first objective lens, wherein objective optical axes of the light-receiving systems are not parallel to each other; and
a first mechanism configured to move the light-receiving systems relative to each other to change an angle formed by the objective optical axes of the light-receiving systems.

2. The ophthalmic microscope of claim 1, further comprising a first controller configured to display, on a display, an image based on output from the first imaging device of at least one of the light-receiving systems.

3. The ophthalmic microscope of claim 2, further comprising a pair of ocular units each including the display and one or more lenses placed on side of a display surface of the display, wherein
the first controller is configured to display an image based on output from the first imaging device of one of the light-receiving systems on the display of one of the ocular units, and display an image based on output from the first imaging device of another of the light-receiving systems on the display of another of the ocular units.

4. The ophthalmic microscope of claim 3, further comprising a second mechanism configured to change a distance between the ocular units.

5. The ophthalmic microscope of claim 3, further comprising a third mechanism configured to change relative orientations of the ocular units.

6. The ophthalmic microscope of claim 3, wherein size of the display surface of the display is 7 inches or less.

7. The ophthalmic microscope of claim 2, further comprising an enlarged image forming unit configured to form an enlarged image of the image based on the output from the first imaging device, wherein
the first controller is configured to display the enlarged image formed by the enlarged image forming unit on the display.

8. The ophthalmic microscope of claim 1, wherein each of the light-receiving systems includes a variable magnification lens.

9. The ophthalmic microscope of claim 1, wherein
the light-receiving systems include their respective lenses to change a focus position,
the ophthalmic microscope further comprising a fourth mechanism configured to move the lenses together.

10. The ophthalmic microscope of claim 9, further comprising:
an auxiliary optical member configured to change a portion of the subject's eye to be observed; and
a second controller configured to control the fourth mechanism in response to a change in the portion to be observed made by the auxiliary optical member.

11. The ophthalmic microscope of claim 1, wherein
the light-receiving systems include their respective deflecting members configured to deflect an optical path,
the ophthalmic microscope further comprising a fifth mechanism configured to move the deflecting members together.

12. The ophthalmic microscope of claim 11, further comprising:
an auxiliary optical member configured to change a portion of the subject's eye to be observed; and
a third controller configured to control the fifth mechanism in response to a change in the portion to be observed made by the auxiliary optical member.

13. The ophthalmic microscope of claim 1, further comprising an optical path coupling member configured to couple an optical path of each of the light-receiving systems with an optical path of the illumination system.

14. The ophthalmic microscope of claim 1, wherein the illumination system is capable of irradiating the illumination light from a direction different from the objective optical axes of the light-receiving systems.

15. The ophthalmic microscope of claim 1, further comprising a pair of second light-receiving systems each including a second objective lens and a second imaging device, configured to guide return light of the illumination light returning from the subject's eye to the second imaging device through the second objective lens, wherein objective optical axes of the second light-receiving systems are not parallel to each other.

16. The ophthalmic microscope of claim 1, further comprising an irradiation system configured to irradiate the subject's eye with light different from the illumination light from a direction different from the objective optical axes.

* * * * *